US005817513A

United States Patent [19]
López et al.

[11] Patent Number: 5,817,513
[45] Date of Patent: Oct. 6, 1998

[54] ANTI GANGLIOSIDE MONOCLONAL ANTIBODIES

[75] Inventors: Ana Maria Vázguez López; Angel Mauro Alfonso Fernández; Rolando Pérez Rodriguez; Amparo E. Macias Abraham; Carlos Manuel Alvarez Valcárcel; Maria Eliana Lanio Ruiz, all of Habana, Cuba

[73] Assignee: Centro de Inmunologia Molecular, Habana, Cuba

[21] Appl. No.: 353,560

[22] Filed: Dec. 9, 1994

[30] Foreign Application Priority Data

Dec. 9, 1993 [CU] Cuba ........................................ 114/93

[51] Int. Cl.⁶ .......................... C12N 5/12; A61K 39/395; C07K 16/30
[52] U.S. Cl. ...................... 435/329; 435/330; 424/130.1; 424/137.1; 424/138.1; 424/141.1; 530/387.1; 530/387.5; 530/387.7; 530/388.1
[58] Field of Search .............................. 530/387.1, 387.5, 530/387.7, 388.1; 435/240.27, 330, 329; 424/130.1, 137.1, 138.1, 141.1

[56] References Cited

FOREIGN PATENT DOCUMENTS

PCT/US88/
04223  6/1989  WIPO .

OTHER PUBLICATIONS

Article entitled: IgM–Induced Specific Antibody Responses: Direct Correlation between Responsiveness and Natural or Induced Recurrence of the Idiotype. Authors: F. Ivars, D. Holmberg, P.–A. Cazenave & A. Coutinho –Published in Scand. J. Immunol. 17, 231–240, 1983.
Article entitled: Perturbation of the Autoimmune Network. Authors: Maurizio Zanetti, Denis Glotz and Joy Rogers –Published in The Journal of Immunology vol. 137, 3140–3146, No. 10, Nov. 15, 1986.
Article entitled: Activation of a Functional Idiotype Network Response by Monoclonal Antibody Specific for a Virus (M–MuLV)–Induced Tumor Antigen. Authors: Thomas J. Powell, Jr., Richard Spann, Meenal Vakil, John F. Kearney and Eddie W. Lamon –Published in the Journal of Immunology, vol. 140, 3266–3272, No. 9, May 1, 1988.
Article entitled: In Vivo Effects of Antibodies Against a High Frequency Idiotype of Anti–DNA Antibodies in MRL Mice. Authors: Dvora Teitelbaum, Joyce Rauch, B. David Stollar and Robert S. Schwartz –Published in The Journal of Immunology, vol. 132, No. 3, Mar. 1984.
Article entitled: Anti–Idiotype Monoclonal Antibody Carrying the Internal Image of Ganglioside GM3. Authors: Saburo Yamamoto, Toshiko Yamamoto, Romaine E. Saxton, Dave S. B. Hoon, Reiko F. Irie –Published in the Journal of the National Cancer Institute, vol. 82, No. 22, Nov. 21, 1990.
Article entitled: Thymus–Dependent Antiidiotype and Anti––Antiidiotype Responses to a Dinitrophenyl–Specific Monoclonal Antibody. Authors: Julie G. Baskin, Tom M Ryan, Meenal Vakil, John F. Kearney and Eddie W. Lamon –Published in The Journal Of Immunology, vol. 145, 202–208, No. 1, Jul. 1, 1990.

Article entitled: The Participation of B Cells and Antibodies in the Selection and Maintenance of T Cell Repertoires. Authors: C. Martinez–A, P. Pereira, M.L Toribio, M.A.R. Marcos, A. Bandeira, A. De La Hera, C. Marquez, P.–A. Cazenave & A. Coutinho –Published in Immunological Reviews 1988, No. 101.

Article entitled: Phase I Trial of the Murine Monoclonal Anti–$G_{D2}$ Antibody 14G2a in Metastatic Melanoma. Authors: Mansoor N. Saley, M.B. Khazaeli, Richard H. Wheeler, Edward Dropcho, Tiepu Liu, Marshall Urist, Donald M. Miller, Sharon Lawson, Pam Dixon, Charles H. Russell, and Albert F. LoBuglio –Published in Cancer Research 52, 4342–4347, Aug. 15, 1992.

Article entitled: Mouse Monoclonal IgG3 Antibody Detecting $G_{D3}$ Ganglioside: A Phase I Trial in Patients with Malignant Melanoma. Authors: Alan N. Houghton, David Mintzer, Carlos Cordon–Cardo, Sydney Welt, Bettina Fliegel, Saroj Vadhan, Elizabeth Carswell, Myron R. Melamed, Herbert F. Oettgen, and Lloyd J. Old –Published in Proc. Natl. Acad. Sci. USA, vol. 82, pp. 1242–1246, Feb. 1985.

Article entitled: Humoral Immune Response in Disease––Free Advanced Malanoma Patients After Vaccination with Malanoma–Associated Gangliosides. Authors: Jacques Portoukalian, Stefan Carrel, Jean–Francois Dore and Philip Rumke –Published in Int. J. Cancer; 49, 893–899 (1991).

Article entitled: Active Specific Immunotherapy in the Treatment of Patients with Cancer. Author: Philip Livingston, MD –Published in Immunology and Allergy Clinics of North America, vol. 11, No. 2, May 1991.

Article entitled: Analysis of the Expression of N–Glycolyl-neuraminic Acid–Containing Gangliosides in Cells and Tissues Using Two Human Monoclonal Antibodies. Authors: Koichi Furukawa, Hiroshi Yamaguchi, Herbert F. Oettgen, Lloyd J. Old and Kenneth O. Lloyd Published in The Journal of Biological Chemistry, vol. 263, No. 34, Issue of Dec. 5, pp. 18507–18512, 1988.

(List continued on next page.)

Primary Examiner—Lila Feisee
Assistant Examiner—Susan Ungar
Attorney, Agent, or Firm—Trask, Britt & Rossa

[57] ABSTRACT

The present invention relates to immunotherapy strategies for the treatment of malignancies. The present immunotherapy strategies have gangliosides as a target. Gangliosides are glycosphingolipids which are present on normal cells and on malignant cells. On malignant cells they are more abundant and expressed in a different organization and conformation. The present invention provides antibodies which recognize these gangliosides, which antibodies are specific, have recurrent idiotypes and have value as immunoregulators. The invention further provides anti-idiotypic antibodies against anti-ganglioside antibodies. These are useful in vaccination strategies.

19 Claims, 12 Drawing Sheets

OTHER PUBLICATIONS

Article entitled: Detection of Gangliosides as N–Glycolyincuraminic Acid–specific Tumor–associated Hanganutziu––Deicher Antigen in Human Retinoblastoma Cells. Authors: Hideyoshi Higashi, Tetsuo Sasabe, Yukio Fukui, Morimasa Maru and Shiro Kato –Published in Jpn. J. Cancer Res. (Gann), 79, 952–956, Aug. 1988.

Article entitled: Density–Dependent Recognition of Cell Surface $GM_3$ by a Certain Anti–Melanoma Antibody, and $GM_3$ Lactone as a Possible Immunogen: Requirements for Tumor–Associated Antigen and Immunogen. Authors: Gustave A. Nores, Taeko Dohi, Masaru Taniguchi and Sen–Itiroh Hakomori –Published in The Journal of Immunology, vol. 139, 3171–3176, No. 9, Nov. 1, 1987.

Article entitled: Aberrant Glycolylation in Cancer Cell Membranes as Focused on Glycolipids: Overview and Perspectives. Author: Sen–itiroh Hakomori –Published in Cancer Research, vol. 45, 2405–2414, Jun. 1985.

Tai et al, JBC, 1987, 262:6803–6807.

Sikorska, J. Biol. Resp. Mod., 1988, 7:327–358.

Johnstone & Thorpe (Immunochem in Practice, Blackwell Scientific Publ, Oxford, 1987, pp. 49–50.

Queen et al. PNAS vol. 86 pp. 10029–10033 1989.

Vick et al. Acta Cytologica 1992. vol. 36 (5) p. 697.

Miyake et al. Cancer Research V. 48 6154–6160 1988.

Shitara et al. Journal of Immunological Methods V. 169 83–92 1994.

Kannagi et al. Japanes Journal of Cancer and Chemotherapy vol. 16 No. 3 1989. p. 679.

ANTI GANGLIOSIDE MONOCLONAL ANTIBODIES

FIELD OF THE INVENTION

The present invention is related to the field of immunology, in particular to the generation and selection of monoclonal antibodies (mAbs) against gangliosides (Ab1s), which antibodies are specific, have recurrent idiotypes and have value as immunoregulators of the immune response against these antigens. It further relates to obtaining anti-idiotypic mabs (Ab2s) generated by immunizing with the anti-ganglioside mAbs.

DESCRIPTION OF THE PRIOR ART

Gangliosides are glycosphingolipids that contain sialic acid and which are expressed in the majority of mammalian cell membranes. Although these antigens are present in normal tissues, they can be found in larger quantities and expressed in a different organization and conformation on the surface of malignant cells (Hakomori, S. (1985), Cancer Res. 45, 2405–2414; Miraldi, F. (1989) Seminars in Nuclear Medicine XIX, 282–294; Hamilton, et al (1993) Int. J. Cancer 53, 1–8).

Some mAbs are capable of recognizing gangliosides only when they are present in high density on the cell surface e.g. mAbs against GM3 (Nores, G. A. et al (1987) J Immunol 139, 3171–3176; Dohi, I. et al (1988), Cancer Res. 48, 5680–5685).

Normal adult tissues only contain NeuAc and not NeuGc-containing gangliosides.

Some human tumors including melanomas, colorectal cancer, retinoblastoma, and non-seminal germinal cell tumors have been reported to have N-glycolyl neuraminic acid containing gangliosides, but they constitute less than 0.05% of the total sialic acid content (Higachi, H. et al (1984) Jpn J Cancer Res (Gann) 75, 1025–1029; Higachi, H. et al (1985) Cancer Res. 45, 3796–3802; Hirabayashi, I. et al (1987) Jpn J Cancer Res (Gann) 78, 1614–1620; Higachi, H. et al (1988) Jpn J Cancer Res (Gann) 79, 952–956; Miyake, M. et al (1990) Cancer 65, 499–505).

Other authors have shown that human mAbs against these antigens did not recognise any of the colorectal tumors or melanomas studied (Furukawa, K. et al (1988) J Biol. Chem. 265, 18507–18512).

Studies of ganglioside content in breast tumors have demonstrated that NeuGc-containing gangliosides constitute approximately 5–11% of the total ganglioside content (Cuban patent application 131-93).

Gangliosides are not good immunogens and in order to elicit an immune response they must be coupled to proteins or incorporated into liposomes or the *Salmonella minnesote* R595 strain. One characteristic of the antibody response to these antigens is that the immunoglobulin class produced is mainly IgM.

Although IgG anti-gangliosides antibodies can be found in humans and mice, the T cell co-operation seems to be non-specific and induced by the adjuvant. Thus, the resulting antibody response after each immunization is short-lived and of low affinity (Livingston, P.O. (1991) Immunology and Allergy Clinics of North America 11, 401–425; Portoukalian, J. et al (1991) Int. J. Cancer 49, 893–899), a typical response against T cell independent antigens (Livingston, P. O. et al (1982) Proc. Natl. Acad. Sci USA 84, 2911–2915; Tai, T. et al (1985) Int J Cancer 35, 607–612; Livingston, P. O. et al (1989) Cancer Res 49, 7045–7050).

Different murine anti-ganglioside mAbs and human mAbs against GD3, GM2 and GD2 have been obtained. Most of them belong to the IgM and IgG3 subclass (Pukel, C. S. et al. (1982) J. Exp. Med. 155, 11133–1147; Cahan, L. D. et al (1982) Proc. Natl. Acad. Sci. USA 79, 76297633; Irie, R. F. et al (1982) 79, 5666–5670; Tai, T. et al (1983) Proc. Natl. Acad. Sci. USA 80, 5392–5396; Hirabayashi, Y. et al (1985) J. Biol. Chem. 260, 13328–13333; Cheung, N. K. V. et al (1985) Cancer Res. 45, 2642; Natoli, E. J. et al (1986) Cancer Res. 46, 4116–4120; Reisfeld, R. and Shulz, G. (1986) Wo 86/00909; Miyake, M. et al (1988) Cancer Res. 48, 6154–6160; Kawashima, I. et al (1988) Int. J. Cancer 41, 267–274; Tai, T. et al (1988) Biochimica et Biophysica Acta 958, 134–138; Tai, T. et al (1988) J. Biochem. 103, 682–687; Yamamoto, S. et al (1990) J. Natl. Cancer Inst. 82, 1757–1760; Yamasaki, M. (1990) U.S. Pat. No. 4,965,198; Kawashima, I. et al (1992) Molecular Immunology 29, 625–632; Kotani, M. et al (1992) Biochimica et Biophysica Acta 1117, 97–103).

Until now, murine anti-ganglioside mAbs have been selected for passive tumor immunotherapy, specificity and subclass.

IgG3 murine mAbs against GD3 and GD2 gangliosides have been used in clinical trials for treatment of melanoma and neuroblastoma patients, respectively and although results have been promising, total or partial remissions have been obtained only in a small number of patients (Houghton, A. N. et al (1985) Proc. Natl. Acad. Sci. USA 82, 1242; Dippold, W. G. et al (1988) Eur. J. Cancer Clin. Oncol. 24, 865; Vadhan-Raj, S. et al (1988) J. Clin. Oncol. 6, 1636; Saleh, M. N. et al (1992) Cancer Res. 52, 4332–4347).

The immunomodulating properties of specific anti-ganglioside mAbs (self, T-independent antigens) have not been studied. Thus, this fact has not been considered when selecting antibodies for tumor immunotherapy.

Self-recognition events are involved in the mechanisms that regulate the immune response. Most of these events are mediated by the recognition of antibody and lymphocyte idiotypes.

Thus, recognition of self antigens is regulated by a dynamic equilibrium of the idiotypic network (Katz, D. H. (1978) In Cell-Cell Recognition. A. S. G. Curtis, ed. Cambridge University Press, Cambridge. p. 4111; Zenetti, M. (1985) Immunology Today 6, 299; Martinez-A, C. et al (1988) Immunological Reviews 101, 191–215).

The study of natural antibodies and their interactions has led to the knowledge of the existence of a highly connected and widely distributed variable region network. This network is different from the antigen controlled "idiotypic cascade" (Kazatchkine, M. D. y Coutinho, A. (1993)), that constitutes the basis of the classical beta anti-idiotypic vaccine concept (internal image).

Beta anti-idiotypic mAbs against anti-ganglioside mAbs have been generated (Yamamoto, et al (1990) J. of the National Cancer Institute 82, 1757–1760; Chapman, P. B. and Houghton, A. N. (1991) J. Clin. Invest. 88, 186–192) to be used in active tumor immunotherapy.

Nevertheless, it has been reported that the selection of anti-idiotypic mAbs based only on the internal image characteristics of the antigen is not adequate for immunotherapy. Selection of anti-idiotypes based on the correlation of the levels of one idiotype with the progression or regression of the disease is of importance for designing an adequate anti-idiotypic immunotherapy (Kohler, H. (1989) WO 89/05309).

In different antigenic models, the regulatory role of certain idiotopes present on antibodies directed against haptens and self-antigens has been demonstrated. These, in the absence of the specific antigen, have the property of activating both the B cell and the T cell network, acting as immunosuppressors or stimulators of the antigenic response in dependence of the T-cell population that they stimulate (Teitelbaum, D. et al (1984) J. Immunology 132, 1282–1285; Zanetti M. et al (1986) J. Immunology 137, 3140–3146; Powell, T. J. et al (1988) J. Immunology 140, 3266–3272; Baskin, J. G. (1990) J. Immunology 145, 202–208; Furuya, A. et al (1992) Anticancer Res. 12, 27–32).

The so-called recurrent idiotypes are the ones capable of activating the complete idiotypic network circuit, generating an antibody response in the absence of the antigen. It has been suggested that these idiotypes are capable of stimulating the helper T-cells (Ivars, F. et al (1983) Scand J. Immunol. 17, 231–240); Forni, L. et al (1980) Proc. Natl. Acad. Sci. USA 77, 1125–1128; Holmberg, D. et al (1982) Immunobiol 162,56–65).

The novelty of the present invention consists in the generation and selection of specific anti-ganglioside antibodies, bearing idiotypes capable of stimulating the immune response against these antigens (recurrent idiotypes). These can be used in the specific active immunotherapy of patients bearing tumors that express the gangliosides and in the generation of anti-idiotypic mAbs against these anti-ganglioside mAbs having the aforementioned properties.

SUMMARY

ANTI GANGLIOSIDES MONOCLONAL ANTIBODIES AND THEIR USE IN THE SPECIFIC ACTIVE IMMUNOTHERAPY OF MALIGNANT TUMORS

The present invention relates to the field of Immunology, particularly the generation and selection of monoclonal antibodies (mAbs) against gangliosides (Ab1s), which antibodies are specific, have recurrent idiotypes and have value as immunoregulators of the immune response against these antigens, and to obtaining anti-idiotypic mAbs (Ab2s) generated by the immunization with the anti-ganglioside mAbs.

Accordingly, this invention provides anti-ganglioside mAbs (Ab1s) with idiotypes capable of inducing an antigen specific response (Ab1') in the absence of the antigen, and methods for their generation.

The objective of this invention also provides anti-idiotypic mAbs (Ab2s) generated by immunization with anti-ganglioside mAbs that have the above mentioned property and are also capable of producing an Ab1' response.

A further important aspect of the invention comprises generating specific anti ganglioside mAbs (Ab1), immunizing mice and other species with the antibodies and selecting those antibodies capable of generating an antigen specific response (Ab1'); generating anti-idiotypic mAbs by immunizing mice or other animal species with the aforementioned anti ganglioside mAbs.

It will be understood that where the term antibodies is used herein that fragments, derivatives and the like which have similar antigen binding properties are also intended. Many ways of arriving at derivatives and/or fragments are known in the art.

Ways of producing derivatives and/or fragments include but are not limited to chemical cleavage and/or (re)assembly, recombinant production of single chain antibodies and/or molecular recognition units (MRU's), CDR-grafting, class switches, etc.

DETAILED DESCRIPTION OF THE INVENTION ISOLATION OF GANGLIOSIDES

Gangliosides were obtained from known natural sources, by a modification of Hakomori's technique (Hakomori, S. et al (1974) Methods in Enzymology, Vol. 32, Part B, p. 350).

PREPARATION OF LIPOSOMAL VESICLES

Liposomal structures containing gangliosides were prepared from DDPC and cholesterol.

Known quantities of DDPC and cholesterol in a chloroformic solution were added to a round bottom flask assuring a phospholipid:cholesterol molar relation between 1:1,5 and 1:2.

Ganglioside dissolved in chloroform:methanol:$H_2O$ (60:30:4,5) was added and the lipid mixture is roto-evaporated in the presence of glass beads.

After eliminating the bulk of the solvents, the fine lipid film is maintained under vacuum during approximately 30 minutes.

Lipid hydration is performed in a PBS solution in a volume allowing a lipid concentration between 2 and 10 mg/ml.

In the final preparation, the DDPC and cholesterol to ganglioside relation is maintained between 40:1 and 20:1 mol to mol.

In the liposomal preparations containing tetanus toxoid toxin, the latter is added at a final concentration between 0.5–1 mg/ml.

The suspension is sonicated in an ultrasonic bath for periods of 5 to 10 minutes, with one minute intervals.

The liposomal preparation is incubated at 45° C. with continuous agitation for 30 to 60 minutes.

When necessary, the non-encapsulated protein is eliminated by gel filtration using a sepharose column CL-4B of 1×65 cm and a flow rate of approximately 20 cm/h.

Elution is-performed in PBS and fractions of 1.5 ml are collected.

CHARACTERIZATION OF THE LIPOSOMAL PREPARATIONS a. Evaluation of Ganglioside Immobilization in the Liposomal Vesicles The amount of gangliosides in the liposomal membrane is estimated using 0.5–1 ml of a liposomal suspension, prepared as previously described, containing the ganglioside labelled with $^{14}C$ (1–2 $\mu Ci$) and performing gel filtration chromatography with sepharose 4B in a 1.5×50 cm column and a flow rate of 7 cm/h. Elution is performed in PBS and 1 ml fractions are collected.

The control of the absorbancy variation between 350 and 500 nm allows the detection of liposomes and micelles in the chromatographic profile, whereas the measurement of the cpm in each fraction allows the estimation of the percent of ganglioside binding in the liposomal preparation, which is between 20–80%.

b. Determination of the % of Proteins Encapsulated in the Liposomal Structure

Using 0.5–1 ml of the non-centrifuged liposomal preparation containing the protein labelled with $^{125}I$ (1–2 $\mu Ci$), a gel filtration chromatography with Sephadex™ G-50 in a 2.5×50 cm column and a flow rate of approximately 7 cm/h was performed.

Elution is performed with PBS and 1 ml fractions are collected.

The estimation of turbidity at 600 nm and of the cpm in each fraction allows for the detection of the presence of the liposomal vesicles and for the estimation of the percent of encapsulated protein in said structures. The amount of encapsulated protein is always below 10 percent.

IMMUNIZATION PROCEDURE FOR GENERATING ANTIBODY RESPONSE (Ab1) AGAINST GANGLIOSIDES

Mice and other mammalian species are immunized with liposomal preparations containing between 20 and 50 $\mu$g of gangliosides per dose. In preparations containing proteins also, these are added in an amount of 5–10 $\mu$g/dose.

Before and during the immunization period, animal blood serum samples are taken for monitoring antibody titers generated in the animals against the gangliosides used as antigens by any known immunoassay method detecting antigen-antibody reaction.

Three days before the first immunization doses, animals were injected with low doses of cyclophosphamide (15 mg/Kg animal body weight) to reduce the suppressor cell activity (Livingston, P. O. et al (1987) J. Immunol 131, 2601; Hoo, D. S. B. et al (1990) Cancer Res. 50, 5358–5354).

The animals can be immunized with various doses of the liposomal preparation at intervals of between 3–4 days and one week.

Liposomal preparations are administered subcutaneously in a volume of 0.1–0.2 ml. Other possible immunization routes are intravenous and intraperitoneal.

Animals receiving from 5–9 accumulative doses of the liposomal preparations at short time intervals develop an antibody response to the ganglioside used as an antigen.

PRODUCTION OF SPECIFIC ANTI GANGLIOSIDE MONOCLONAL ANTIBODIES (mAbs)

Mice with serum antibody titers against gangliosides receive a new immunization with the liposomal preparations, three days before obtaining the antibody producing cells. Spleen cells should be preferentially used although other antibody producing cells may be selected.

These cells are fused with myeloma cells that give the hybrid cells or hybridomas the property of in vitro and in vivo reproduction. Cellular fusion may be performed by any of the known methods.

The antibodies produced by the hybridomas are tested by immunoassay methods, preferably by an immuno-enzymatic assay in which hybridoma supernatants react with the gangliosides and the antigen-antibody binding is detected using a second enzyme labelled antibody capable of binding to the antibody under adequate conditions.

Once the desired hybridoma is selected and cloned (i.e. limiting dilution) at least twice, the resulting mAb can be produced in vitro in an adequate medium, during an appropriate period, followed by the recovery of the desired antibody from the supernatant.

The selected medium and the adequate culture time period are known or easily determined.

Another production method comprises the injection of the hybridoma in animals (i.e. in syngeneic mice). The hybridoma will cause the formation of non-solid tumors, which will produce a high concentration of the desired antibody in the blood stream and the peritoneal exudate (ascites) of the host animal.

The mAbs obtained have different specificities for the different gangliosides.

IMMUNIZATION PROCEDURES FOR OBTAINING ANTI IDIOTYPIC (Ab2) AND ANTI-ANTI-IDIOTYPIC (Ab1') ANTIBODY RESPONSE TO ANTI GANGLIOSIDE mAbs

Mice and other mammalian species are immunized with 25–200 $\mu$g doses of purified anti-ganglioside mAbs with or without adjuvant and optionally coupled to a transporting protein.

Animals receive 3–6 doses of anti ganglioside mAbs at 15 to 30 days intervals between doses. Possible immunization routes are intraperitoneal, subcutaneous, endovenous or a combination of these.

Before and during the immunization period animal blood serum samples are taken and Ab2 and Ab1' antibody level response are determined by any known immunoassay methods. Animal serum dilutions are incubated with the anti-ganglioside mAb used as immunogen, or other anti-ganglioside mAbs not used in the immunization protocol or the gangliosides.

Experiments were also performed to define the capacity that the serum of the immunized animals has for blocking the binding of the anti-ganglioside mAb used as immunogen to its antigen.

Thus, those specific anti-ganglioside mAbs capable of connecting to the idiotypic network generating an anti-idiotypic response (Ab2) and producing an anti-anti-idiotypic antibody response (Ab1') in the absence of the antigen were selected. In other words anti-ganglioside mAbs bearing idiotypes capable of stimulating an anti-ganglioside immune response (recurrent idiotypes) were selected.

ANTI-IDIOTYPIC mAb PRODUCTION AGAINST ANTI GANGLIOSIDE mAbs BEARING RECURRENT IDIOTYPES

Mice with high anti-ganglioside Ab2 antibody titers receive a re-immunization with the mAb used as immunogen three days before obtaining the antibody producing cells to be fused with the myeloma cells as previously described.

Hybridoma supernatants obtained from the fusion are tested by any of the known immunoassay methods. Supernatants are incubated with the mAb used as immunogen and with other anti-ganglioside mAbs not used in the immunizations.

The capacity of the hybridoma supernatant of blocking the binding of the anti-ganglioside mAb used as immunogen to its antigen is determined by incubating the supernatants with adequate dilutions of the anti-ganglioside mAb followed by incubation of said antibody with its antigen.

The selected hybridomas are cloned at least twice and the resultant mAbs are produced in vitro and in vivo as described above.

The anti-idiotype mAbs obtained recognise the anti-ganglioside mAbs and can optionally possess (beta-type) the capacity of blocking the binding of the anti-ganglioside mAb to its antigen.

IMMUNIZATION PROCEDURE FOR OBTAINING ANTIBODY RESPONSE AGAINST GANGLIOSIDES USING ALPHA TYPE ANTI-IDIOTYPIC mAbs

Mice or other mammals are immunized with alpha anti-idiotypic mAbs. These mAbs can be coupled to a transporting protein before being used as immunogen.

Each animal receives from 3–5 doses of 25–200 µg of the alpha anti-idiotypic mAb, at time intervals of 15–30 days between doses.

Immunization routes can be intraperitoneal, subcutaneous, endovenous or a combination of these.

Animal blood samples are obtained before and during the immunization protocol and the serum antibody titers against the different gangliosides are monitored using any of the known immunoassay methods.

The administration to animals of alpha anti-idiotypic mAbs, produced by the immunization with anti-ganglioside mAbs highly connected to the idiotypic network, can induce a vaccine effect, generating an antibody response against the gangliosides (Ab1').

EXAMPLE 1

Generation of Antibody Response (Ab1) to NeuAcGM2 by an Atypical Immunization Protocol: Short Time Intervals and Cumulative High Doses Female balb/c mice, 6–8 weeks old received an intraperitoneal injection of cyclophosphamide (15 mg/Kg) in phosphate buffer saline solution (PBS) (Livingston, P. O. et.al. (1983), J. of Immunol. 131, 2601; Hoo, D. S. B. et. al. (1990) Cancer Res. 50, 5358). Three days later the mice were immunized subcutaneously with a liposomal preparation containing 50 µg of NeuAcGM2 in 0.2 ml PBS.

The animals received 5 doses at 3–4 days intervals followed by 4 additional weekly doses, resulting in a total accumulative doses of 450 µg. Animal serum samples were obtained before starting immunization and one week after the fifth and ninth doses.

Antibody level in mice serum was detected by an indirect, immuno-enzymatic assay (ELISA) performed on polyvinyl chloride activated plates (ICN-FLOW) with immobilized NeuAcGM2, according to the following method:

Fifty microliters of NeuAcGM2 in methanol (4 µg/ml) were added to each well. Methanol was evaporated by placing theplates at 37° C. during one hour. Next, 150 µl/well of buffer TRIS-HCl 0.05M pH 7.8 containing 1% bovine serum albumin (BSA) were added and plates incubated at 37° C. for 30 minutes.

Fifty microliters/well of serum diluted in PBS were then added and plates were incubated at 37° C. for 90 minutes.

Wells were washed 4 times with 200 µl of PBS and 50 µl of alkaline phosphatase anti mouse immunoglobulin conjugates antiserum, adequately diluted were added. After washing with PBS, the wells were incubated with 100 µl of substrate buffer (1 mg/ml of p-nitrophenylphosphate diluted in diethanolamine buffer pH 9.8). Absorbance was measured at 405 nm in an ELISA reader.

The mice showed no antibody response to NeuAcGM2 after the first 5 immunization doses. Nine cumulative immunogenic doses were required to obtain a detectable antibody response in 50% of the immunized animals (FIG. 1).

EXAMPLE 2

Generation of Antibody Response (Ab1) to NeuGcGM3

Female Balb/c mice, 6–8 weeks old received an intraperitoneal injection of cyclophosphamide (15 mg/Kg) three days before the first immunization with a liposomal preparation containing 50 µg of NeuGcGM3 and 5 µg tetanus toxoid per dose in a 0.2 ml volume.

The animals received 5 doses of the immunogenic preparation at 3–4 days intervals followed by 2 additional weekly doses. Animal serum samples were obtained before and after starting the immunization protocol. Antibody level in mice serum was detected as in Example 1. Mice with no natural response to NeuGcGM3 produced antibodies to NeuGcGM3 after receiving various doses of the immunogen (FIG. 2), up to an cumulative doses of 350 µg.

EXAMPLE 3

Generation of mAb Against NeuAc- and NeuGc-containing Monosialogangliosides

Monoclonal antibodies were generated immunizing Balb/c mice, by the procedures described in Examples 1 and 2, with liposomal preparations containing NeuAcGM1, NeuAcGM2, NeuAcGM3 and NeuGcGM3 gangliosides.

Three days before fusion, the animals were re-immunized with the respective liposomal preparations. Afterwards, mice spleens were removed and a cellular suspension prepared by pressing the tissue through a stainless steel sieve or perfusing the spleen.

Fusion was performed by the method described by Kohler and Milstein (1975, Nature (Lond) 256, 495–497), with slight modifications.

Murine spleen cells were fused with the cells of the non-secreting murine myeloma P3/X63 Ag8 6.5.3., in a ratio of 10:1, in 0.5 ml of fusion medium containing 42% polyethylene glycol in RPMI-1640 medium.

After fusion, cells were cultivated in a HAT (hypoxanthine-aminopterin and thymidine) selective medium at 37° C. in a 5% CO2 humid atmosphere.

Ten to fifteen days after fusion evaluation of presence of antibodies in hybridoma supernatant was performed using the ELISA method previously described in Example 1.

Selected hybridomas recognizing the ganglioside of interest were cloned twice by the limiting dilution method in the presence of conditioning cells.

Specificity of antibodies produced by the selected hybridomas was determined using a battery of glycolipids by indirect ELISA and by a modification of the fine layer immuno-staining chromatography technique described by Magnani et. al. (Anal. Biochem. 109, 399402, 1980).

Glycolipids were separated by high performance thin layer chromatography using as chromatography solvent chloroform/methanol/potassium chloride 0.25% (50/40/10, v/v/v).

The plate was air dried and plastified with 0.5% polyisobutyl methacrylate (Aldrich Chemical Co. Ltd., Gillingham, England) in hexane. Once dried, the plate was blocked with 1% BSA in TRIS/HCl 0.05M pH 7.8–8.0 buffer solution during 30 minutes at room temperature. The plate was then incubated with the anti-ganglioside mAbs (tissue culture supernatant) overnight at room temperature.

Afterwards, the plate was washed four times with PBS and incubated for three hours at room temperature with an alkaline phosphatase conjugated anti-mouse immunoglobulins antiserum (Jackson Immunoresearch Laboratories Inc.) diluted 1:5000 in TRIS-HCl buffer solution containing 1% BSA.

The plate was washed in similar conditions and incubated during one hour at 37° C. with the substrate solution containing 0.1% 5'-bromo-4'-chloro-3'-Indolylphosphate dissolved in glycine buffer 0.1M pH 10.4, ZnCl2 1 mM, MgCl2 1 mM. The reaction was stopped by washing with water.

Selected clones were then intraperitoneally injected (0.5–1×106 cells in 0.2 ml) to Balb/c mice previously inoculated with 2,6,10,14-tetramethyl pentadecane, although other ascitogenic agents can be used.

Four IgM mAbs recognizing different monosialo-gangliosides were obtained (table 1).

A3 mAb recognizes preferentially NeuAcGM2 and NeuAcGM1 and reacts moderately with NeuAcGM3, all with N-acetyl sialic acid residues. (The hybridoma cell line producing A3 antibody has been deposited at ECACC under no. 94113023 under the provisions of the Budapest Treaty, deposited Nov. 30, 1994 with the Center for Applied Microbiology and Research Authoruty (European Collection of Animal Cell Cultures, Porton Down, Salisbury, Wiltshire SP4, 0JG, The United Kingdom).

Glycolipids with addition (GD1b or GD1a) or loss (Gg4Cer) of an N-acetyl sialic acid residue do not react with A3 mAb.

The loss of a terminal galactosamine, such as in NeuAcGM3 ganglioside, reduces the reactivity of this antibody.

These results added to the fact that the loss of the terminal galactose did not affect the recognition of the NeuAcGM2 indicates that the epitope recognized by A3 mAb could be the trisaccharidic sequence GalNAcβ1-4 (NeuAcα2-3)Gal.

E1 mAb showed highly restricted binding specificity detecting only NeuAcGM2. (The hybridoma cell line producing E1 antibody has been deposited at ECACC under no. 94113025

Glycolipids with loss of one terminal galactosamine i.e. NeuAcGM3, or addition of a terminal galactose i.e. NeuAcGM1 were not recognized by this mAb.

E1 mAb can distinguish between N-acetyl and N-glycolyl groups. Thus, the terminal galactosamine and the N-acetyl neuraminic acid linked to the internal galactose are involved in the antibody recognition.

F6 mAb predominantly reacts with NeuAcGM1, moderately recognizes GD1b and has low reactivity with the Gg4Cer glycolipid. (The hybridoma cell line producing F6 antibody has been deposited at ECACC under no. 94113026)

The fact that it does not recognize gangliosides with absence of terminal galactose (GM2 and GD2) nor GD1a, that has an N-acetyl neuraminic acid linked to the terminal galactose, suggests that this external monosaccharide is important for the binding to the antibody.

Moreover, glycolipids that lack the N-acetyl neuraminic acid linked to the internal galactose (Gg4Cer) react weakly with the F6 mAb, while the addition of an N-acetyl sialic acid residue to this position (GD1b compared to GM1) changes moderately antibody reactivity.

All these facts suggest that the tetrasaccharidic structure Galβ1 -3GalNAcβ1-4(NeuAcα2–3)Gal is involved in the antigenic recognition.

P3 mAb binds specifically to the N-glycolyl neuraminic acid linked to the internal galactose of the gangliosides. (The hybridoma cell line producing P3 antibody has been deposited at the Centre for Applied Microbiology and Research Microbiological Research Authority (European Collection of Animal Cell Cultures), Porton Down, in accordance with the Budapest Treaty, on Nov. 30, 1994 as Deposit ref. 94113026).

EXAMPLE 4

P3 mAb Tumor Recognition

Tissues were fixed in a 10% formaline buffer solution and dehydrated, cleared and paraffin embedded. Histopathology was evaluated on H&E stained tissue sections.

Consecutive sections from histopathologically assessed blocks were used for immunostaining with the biotin streptavidin-peroxidase complex method previously described (Hsu, S. M. and Raine, L. (1981) J. Histochem. Cytochem. 29:1349–1353).

De-paraffinized and rehydrated tissue sections were treated with 3% $H_2O_2$ (methanol solution) for 30 minutes to eliminate endogenous peroxidase activity.

Sections were incubated with P3 mAb (tissue culture supernatant) for one hour at room temperature. Biotinylated sheep anti-mouse immunoglobulins and biotin streptavidin peroxidase complex (DAKO A/S) were then added for 30 minutes each at room temperature.

Between incubations, the sections were washed with TRIS saline buffer solution.

Peroxidase reaction was developed using a solution containing 5 ml of TRIS saline buffer solution, 5 µl of 30% $H_2O^2$ and 3 mg of 3—3 diaminobenzidine.

Slides were washed with tap water, counterstained with Mayer's Hematoxiline, a mounting medium containing balsam was added and coverslips were placed.

Enzyme reaction produces a brown coloring classified as follows: no reaction (–), weak (+), moderate (++) and strong ( +++).

A positive reaction on ductal infiltrating breast carcinoma, breast cancer metastasis lymph nodes and breast adenosis tissue sections was obtained using P3 mAb.

The antibody shows a fine granular cytoplasmic and membrane reaction. No reaction was observed with the rest of the malignant and benign tumor tissues studied (Table 2).

EXAMPLE 5

Anti-idiotypic (Ab2) Response to IgM Anti-ganglioside Antibodies in a Syngeneic Model Two different immunization protocols were performed with Balb/c mice receiving four to six 25 µg mAb intraperitoneal doses every 15 days. A3, P3 and E1 mAbs were injected alone or coupled to KLH, as a transporting protein in presence of Freund's complete adjuvant in the first doses and Freund's incomplete adjuvant in the following doses.

Mice serum samples were obtained before and 7 days after the immunizations.

The presence of Ab2 response in mice serum was determined by ELISA. ELISA plates (high binding COSTAR) were incubated overnight at 4° C. with 10 µg/ml of the different anti-ganglioside mAbs used as immunogens in carbonate-bicarbonate buffer pH 9.8.

Plates, after washing with PBS containing 0.05% Tween 20, were blocked with the same buffer containing 1% BSA during one hour at 37° C.

Washing step was repeated and 50 µl/well of the different serum dilutions were added. After incubating for 2 hours the plates were washed again and alkaline phosphatase goat anti-murine IgG Fc region conjugate antiserum was added. After washing, the substrate solution was added as in the ELISA previously described.

When mice were immunized with A3 and E1 Mabs alone an Ab2 response in mice serum was not obtained, whereas the administration of these same antibodies conjugated with KLH and in presence of adjuvant caused a strong IgG type anti-idiotypic reaction (Ab2) specific for the mAb used as immunogen.

Meanwhile, P3 mAb (anti-NeuGcGM2/NeuGcGM3) showed an IgG type Ab2 response when used alone (antibody title 1:1000) that increased when coupled to KLH and in presence of adjuvant (1:50000) (Table 3).

The IgG type anti-idiotypic (Ab2) response to these mAbs indicates the participation of the helper T cells in this antibody response.

These IgM type Ab1 anti-ganglioside mAbs, physiologically administered, show different capacity to produce an Ab2 response in a syngeneic model, thus showing different capacities of connection to the T cell idiotypic network in Balb/c mice.

Nevertheless, when coupled to KLH and in presence of adjuvant all are capable of connection with the T and B cell idiotypic network generating a strong Ab2 response.

EXAMPLE 6

Generation of anti-anti-idiotypic (Ab1') response to IgM type anti-ganglioside mAbs in a syngeneic model: specific antigen independent antibody response.

E1 (anti-NeuAcGM2) and P3 (anti NeuGcGM3/NeuGcGM2) mAbs conjugated to KLH were used to immunize 6–8 weeks old female Balb/c mice.

Animals received 4–≠doses of 25 μg doses of mAb conjugated to KLH at 15 days intervals in presence of Freund's complete adjuvant the first dose and Freund's incomplete adjuvant the remaining doses.

Animal serum samples were obtained before and during the immunizations.

The Ab1 'antibody levels were determined by an indirect ELISA method as described in Example 1.

Immunization with liposomes required at least 9 doses to obtain an antibody response against NeuAcGM2. In contrast, when immunization was performed using the E1 mAb coupled to KLH only 3 doses were needed to obtain an anti-ganglioside antibody response (FIG. 3).

Likewise, immunization with P3 mAb coupled with KLH produced an antibody response against NeuGcGM2 (Ab1') in 6 of the 8 animals immunized (FIGS. 4 and 5).

These results indicate that these antibodies, that physiologically or conjugated to KLH, were capable of generating an Ab2 type response, also have the capability of generating an Ab1' response in a syngeneic model. Indicating that they have recurrent idiotopes, i.e., idiotopes capable of generating a specific antigen independent antibody response.

EXAMPLE 7

Generation of Hybridomas Producing Antiganglioside mAbs by Immunizing Balb/c Mice with the P3 mAb Female Balb/c mice, 6–8 weeks old were immunized with the P3 mAb conjugated with KLH using the immunization protocol described in Example 6.

One mouse with serum Ab1' type antibody titers against NeuGcGM3 was used to fuse its spleen cells with the myeloma cell line P3/X63 Ag8 6.5.3. using the fusion technique described in Example 3.

Hybrid cell clones producing antibodies recognizing preferentially monosialogangliosides (FIG. 6) were obtained from this fusion. In contrast, immunization with liposomes containing NeuGcGM3 and tetanus toxoid produced mainly clones that produce antibodies that recognize all the gangliosides to which they were tested (FIG. 7). Thus, immunization with the P3 Mab may cause the activation of clones producing antibodies against gangliosides similar or qualitatively superior to those obtained immunizing with the ganglioside included in liposomes.

EXAMPLE 8

Generation of an Anti-idiotype Antibody Against E1 mAb in a Syngeneic Model

Female Balb/c mice, 6–8 weeks old, were immunized with E1 Mab (anti NeuAcGM2) coupled to KLH using the immunization protocol described in Example 4.

Splenocytes from a mouse with high serum levels of Ab2 antibodies against E1 mAb were fused with the P3/X63 Ag8 6.5.3. myeloma cell line following the fusion method described in Example 3.

An anti-idiotypic mAb of the IgG2a subclass was obtained. It was demonstrated that this was an alpha anti-idiotypic mAb since it was not able to inhibit the binding of E1 mAb to its antigen (NeuAcGM2) (FIG. 8).

This B7 anti-idE1 mAb showed to be highly connected to a group of Ab1 anti-ganglioside antibodies to which it was tested. It reacted with the E1 mAb used as immunogen and the P3 (anti NeuG-cGM3/Neu GcGM2) and A3 (anti NeuAcGM2/NeuAcGM1/NeuAcGM3) mAbs (FIG. 9). The hybridoma cell line producing B7 anti-idE1 was deposited at ECACC under no. 94113024.

Another anti-idiotypic mAb of the IgG2a subclass was also obtained. This was a paratopic (beta or Gamma) anti-idiotypic mAb since it was able to inhibit the binding of the E1 mAb to its antigen (NeuAcGM2) (FIG. 10). This anti-idE1 (F2) mAb was very specific to the E1 mAb used as an immunogen. It does not react with other anti-ganglioside antibodies, such as the P3 and A3 mAbs (FIG. 11).

EXAMPLE 9

Antibody Response Against NeuAcGM2 After Immunization with B7 Anti idE1-Mab in a Syngeneic Model (Vaccine Effect)

B7 Anti-idE1 mAb was coupled to KLH and used to immunize 6–8 weeks old female Balb/c mice at 21 days intervals with a dose of 50 μg of Mab. The animals received three doses of KLH conjugated to B7 anti-idE1 Mab. The first dose in presence of Freund's complete adjuvant and the other two doses in Freund's incomplete adjuvant.

Serum samples were taken before and after the immunizations. Antibody response to NeuAcGM2 was determined by an indirect ELISA method as described in example 1.

As shown in FIG. 12, the alfa B7 anti-idiotypic mAb, was capable of generating antibody an response against NeuAcGM2 ganglioside in the syngeneic model.

Figure 1:
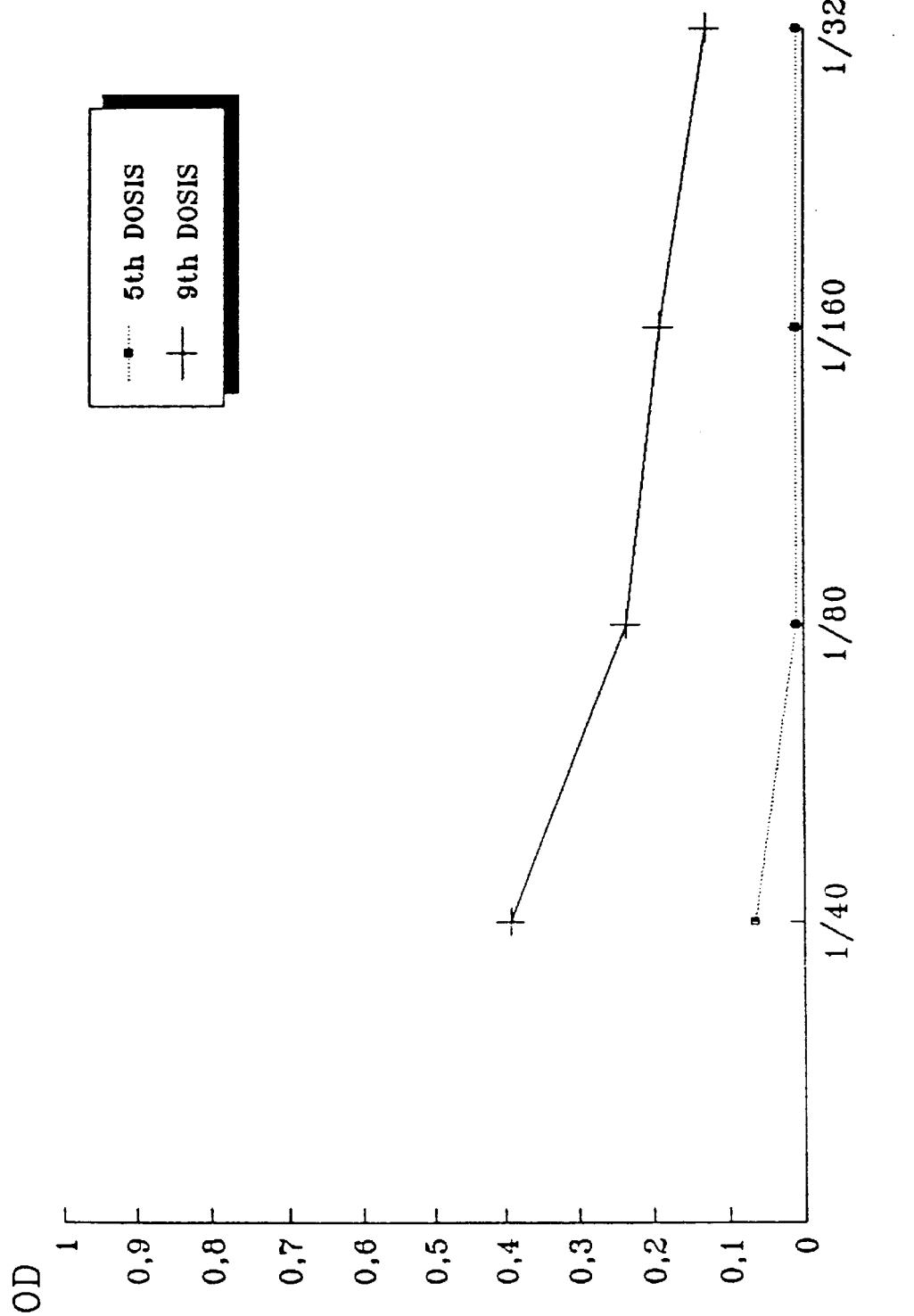
FIG. 1: shows the serological antibody response against NeuAcGM2 measured by ELISA in the serum from a mouse immunized with the ganglioside incorporated into liposomes. The antibody response was measured after the fifth and ninth doses.
Figure 2:
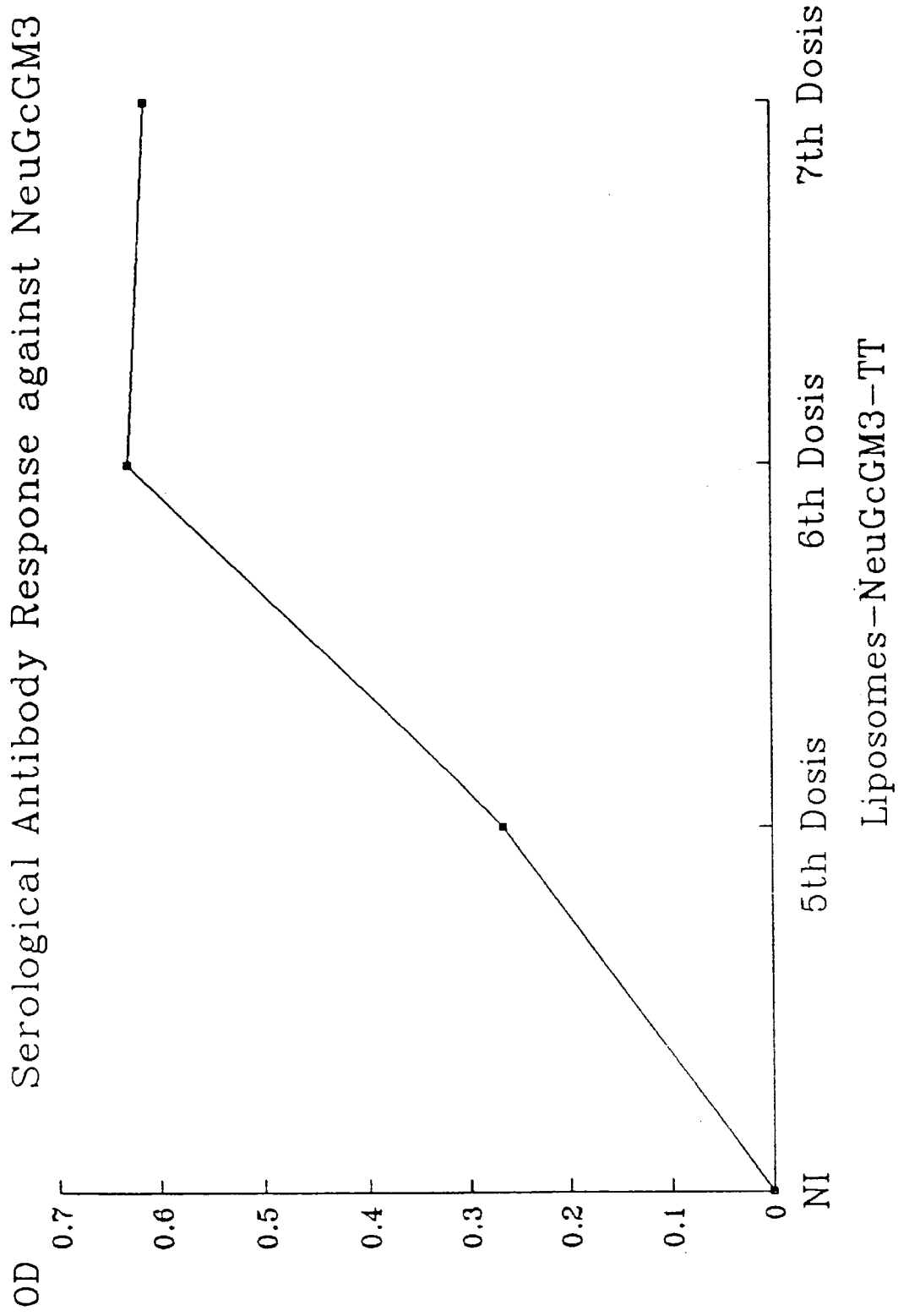
FIG. 2: shows the serological antibody response against NeuGcGM3 in the serum from a mouse immunized with the ganglioside incorporated in liposomes that contained tetanus toxoid. The antibody response was measured by ELISA in the serum of the mice diluted 1/80, after the animal received the 5th and 7th doses of the immunogen.
Figure 3:
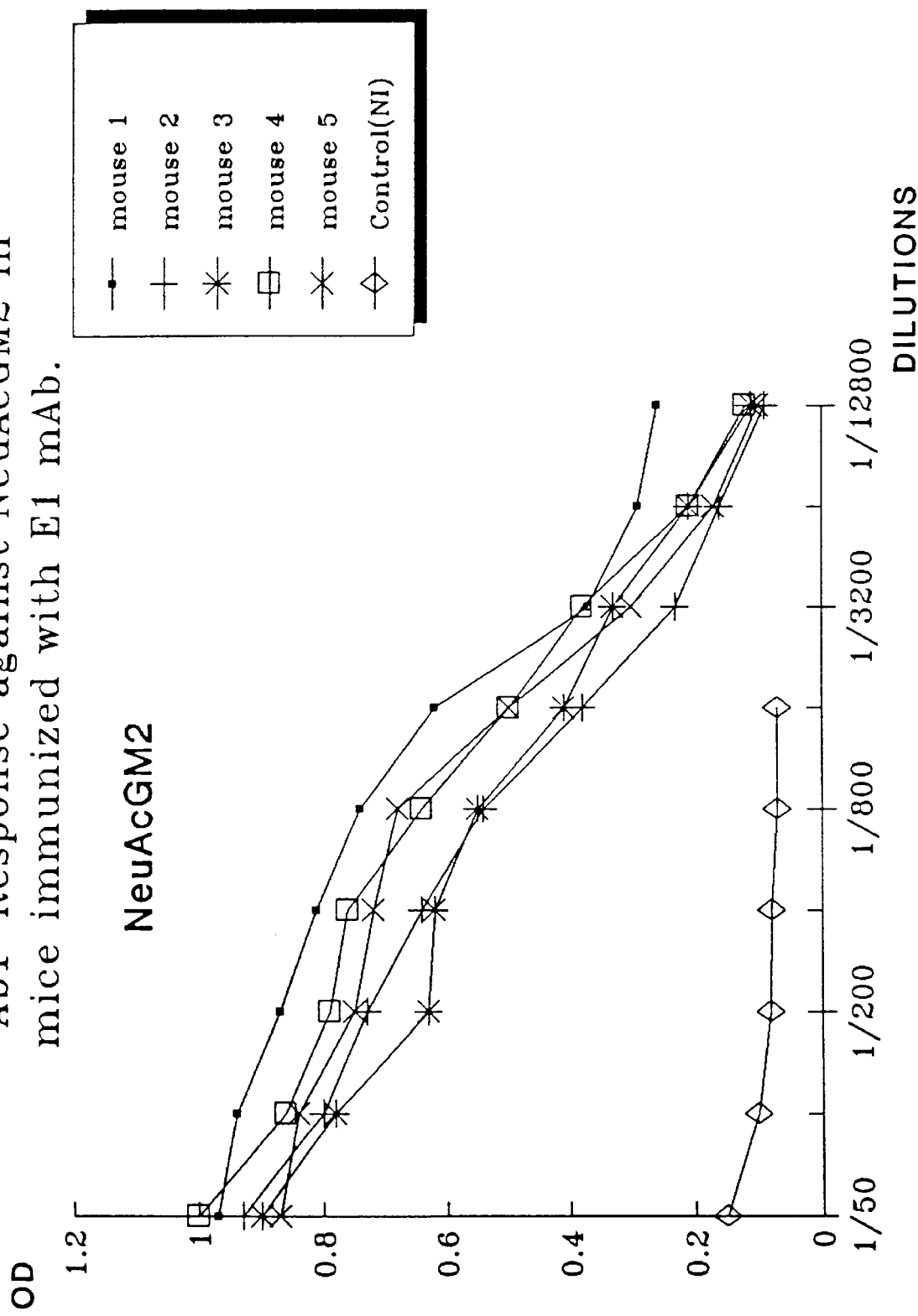
FIG. 3: shows the serological anti-anti-idiotypic (Ab1') response against NeuAcGM2 generated in Balb/c mice immunized with E1 mAb coupled to KLH in the presence of Freund adjuvant. Ab1' antibody response was measured by an indirect ELISA before and after the animal received three doses of the mAb.
Figure 4:
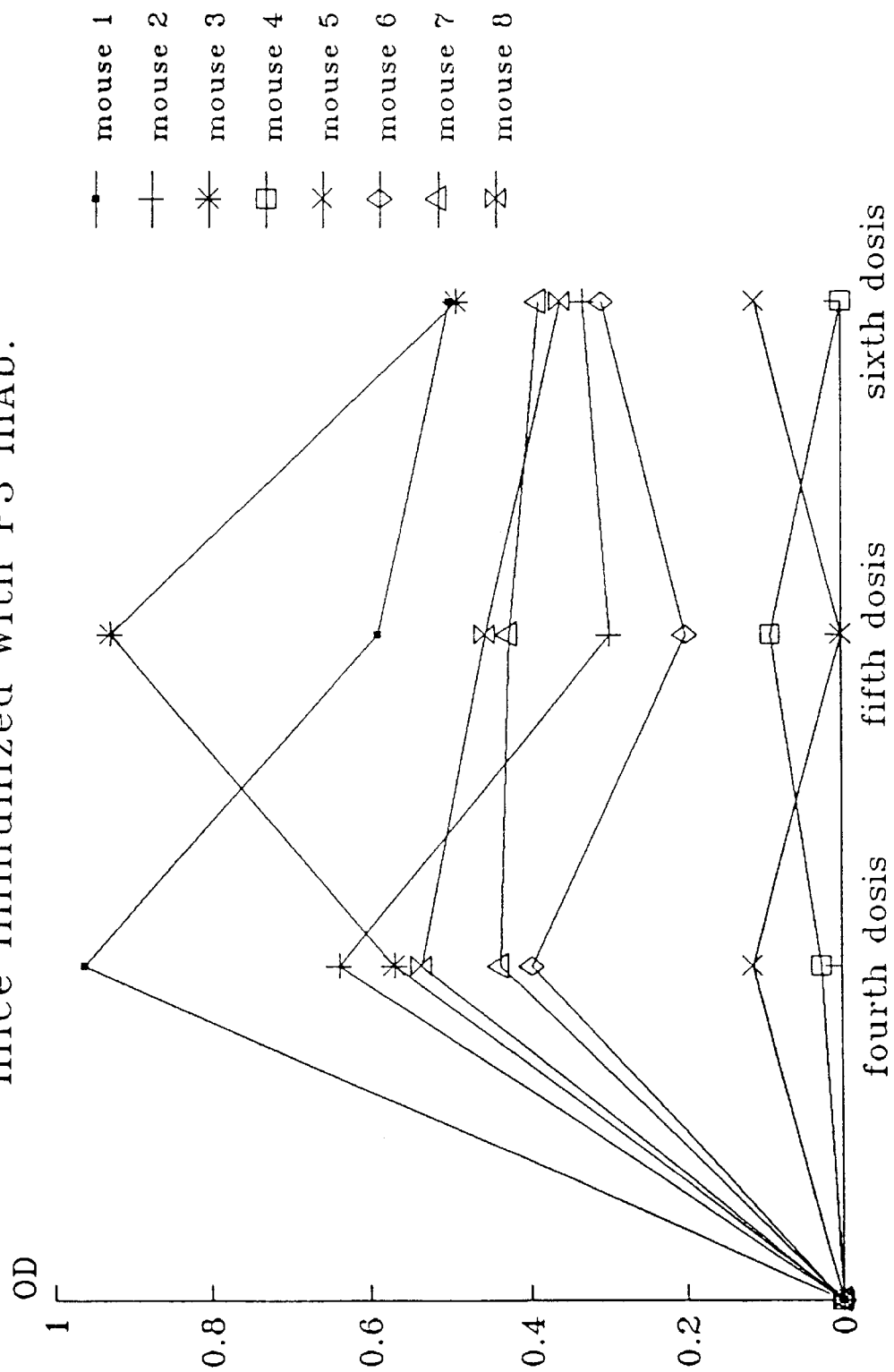
FIG. 4 and 5: show the anti-anti-idiotypic (Ab1') response against NeuGcGM3 measured by an indirect ELISA in the serum of mice immunized with P3 mAb coupled to KLH, and in the presence of Freund adjuvant. The Ab1' response was measured before and after the animals received the fifth and sixth doses of the mAb.
Figure 5:
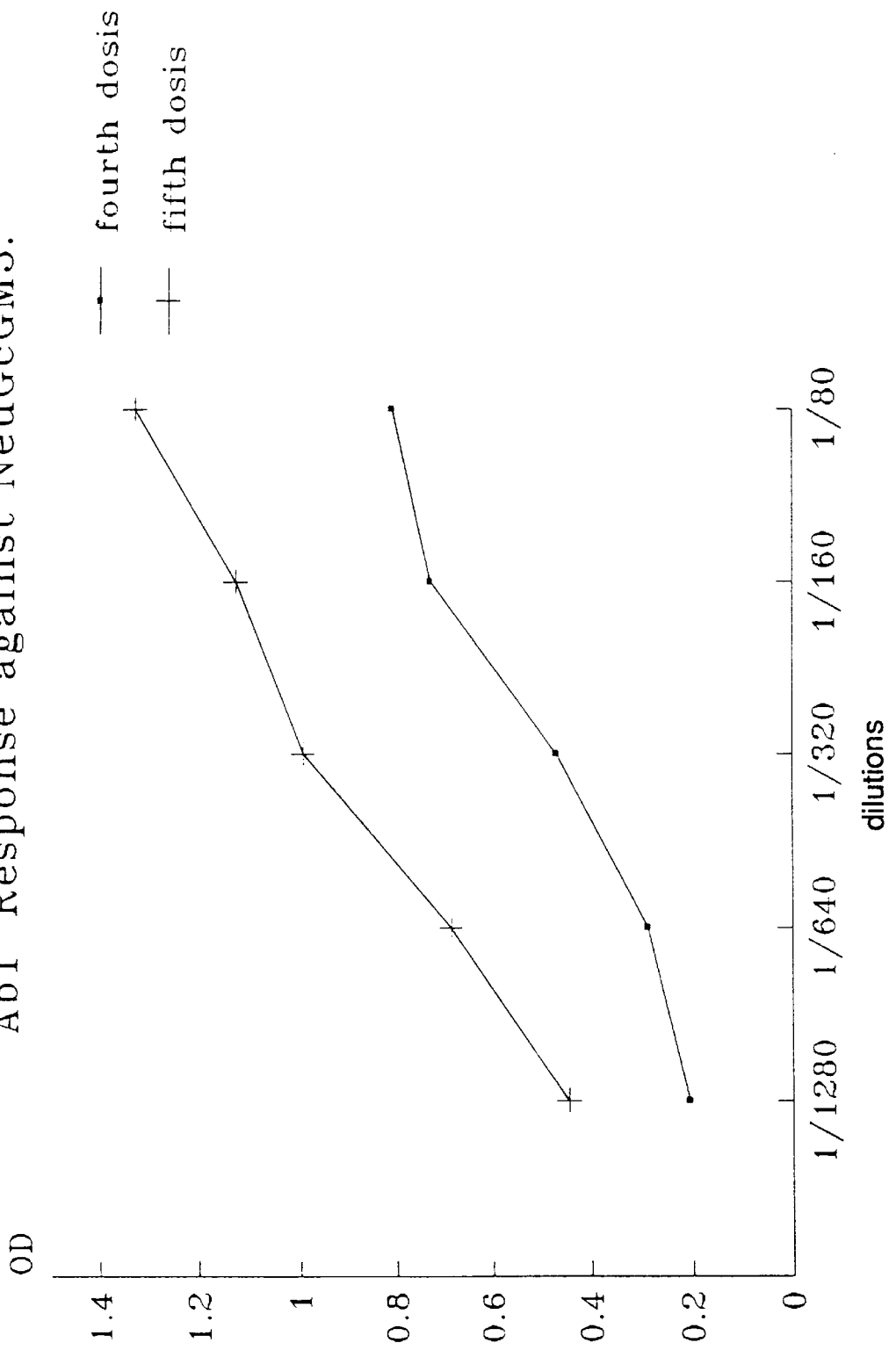
Figure 6:
FIG. 6: Shows the recognition pattern of hybridomas supernatants against different gangliosides. Hybridomas were obtained from the fusion of X63 Ag8 6.5.3 murine myeloma cells with the spleen cells from a mouse immunized with P3 Mab.
Figure 7:
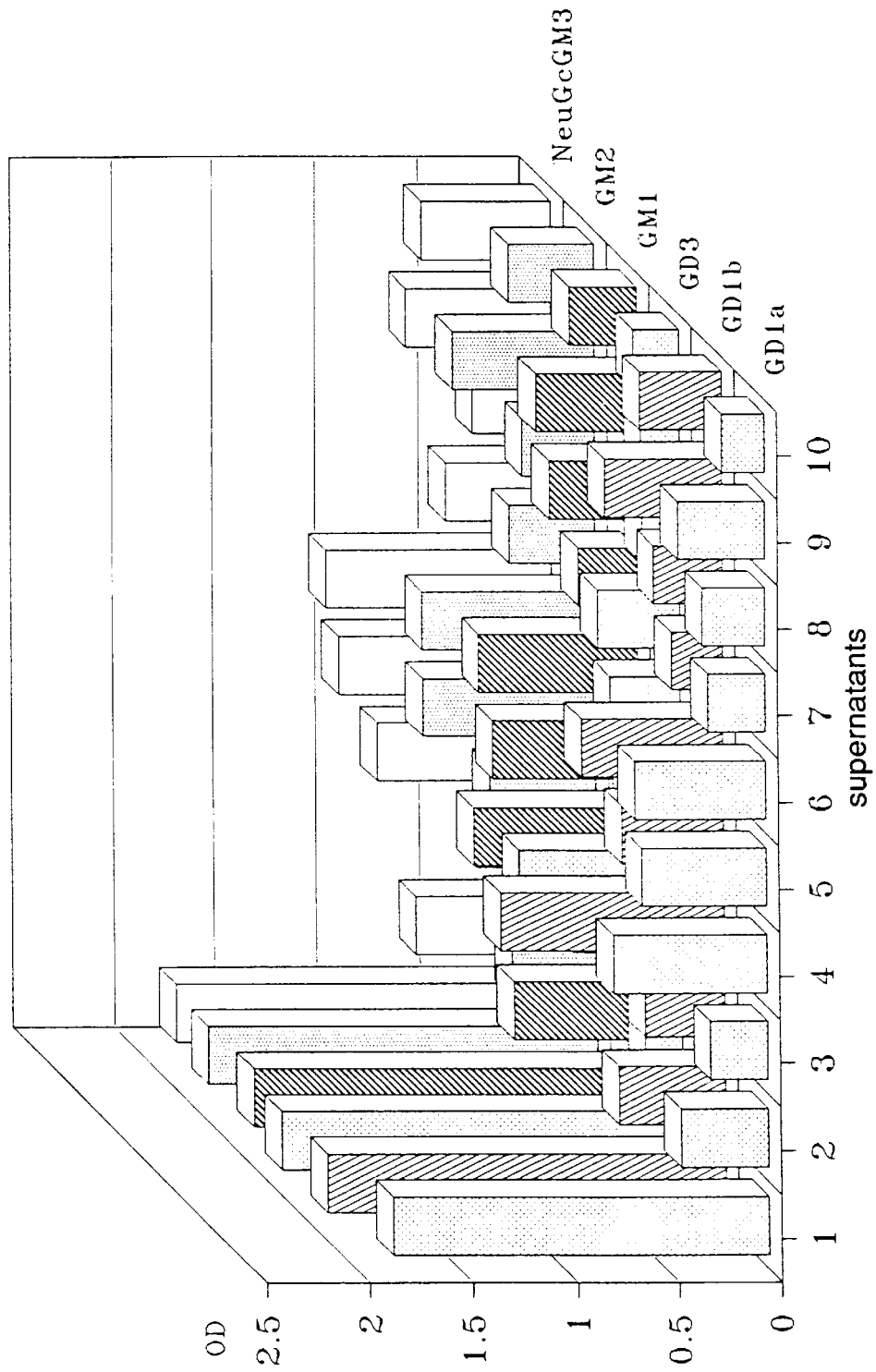
FIG. 7: shows the recognition pattern of hybridomas supernatants against different gangliosides, obtained by the fusion of X63 Ag8 6.5.3 myeloma cells with splenocytes from a mouse immunized with NeuGcGM3 incorporated in liposomes which contained tetanus toxoid.
Figure 8:
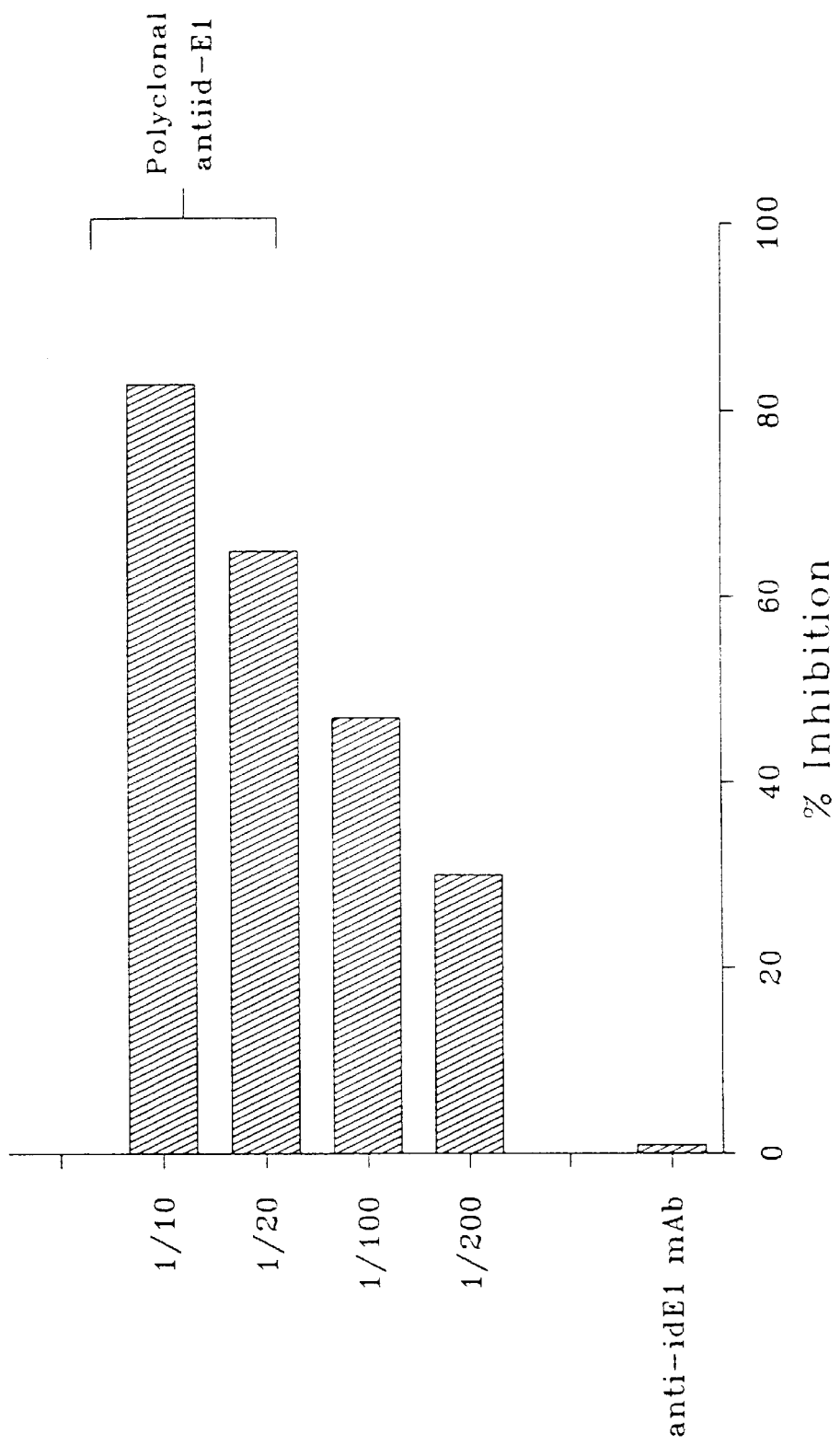
FIG. 8: shows the results of an inhibition assay where the E1 mAb was incubated with the B7 anti-idE1 Mab or with different dilutions of a mouse polyclonal anti-idE1 antiserum, and later the binding of E1 mAb to NeuAcGM2 were measured by ELISA and the percent (%) of binding inhibition was calculated.
Figure 9:
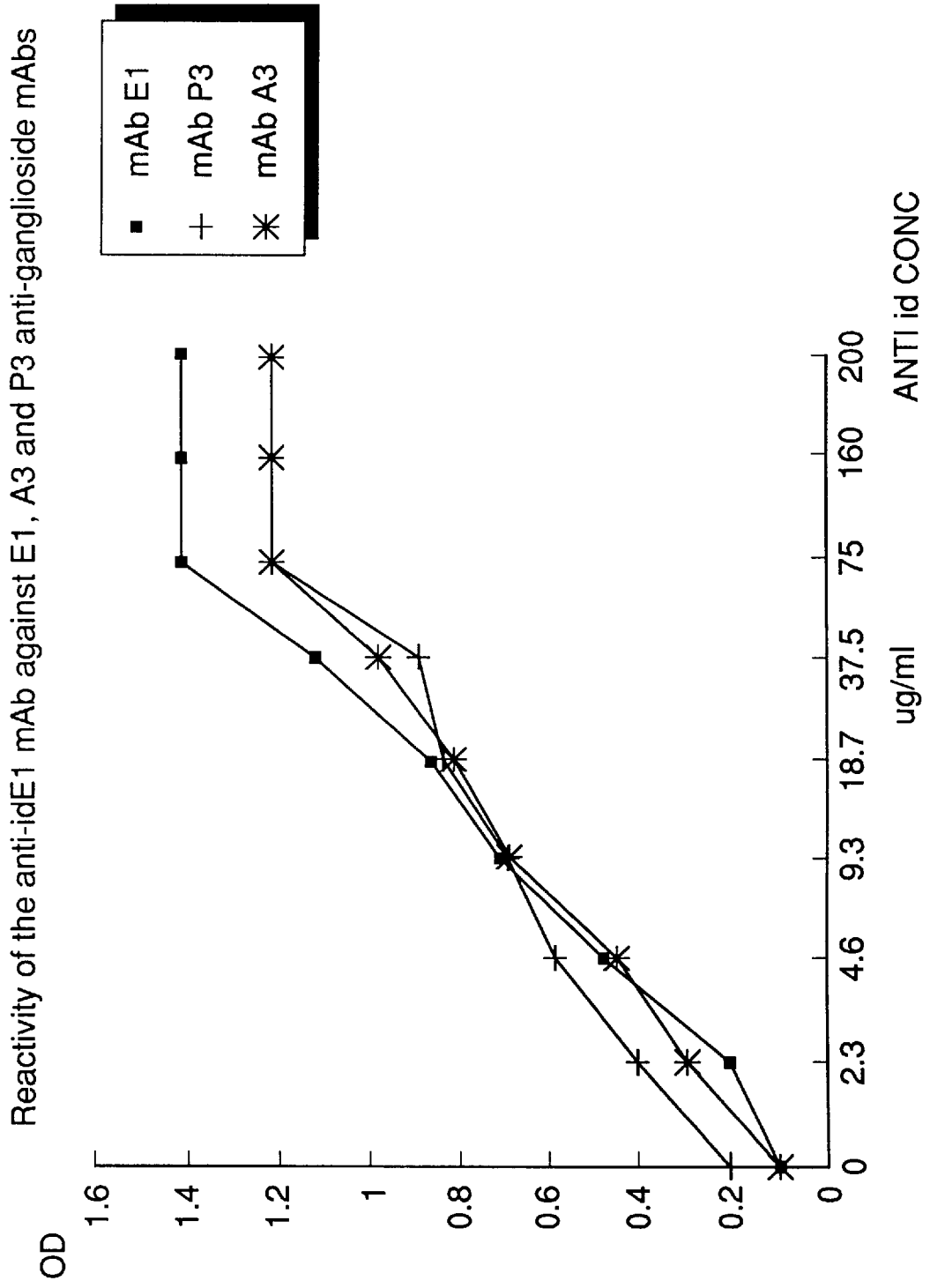
FIG. 9: shows the reactivity of the B7 anti-idE1 Mab against E1, A3 and P3 anti-ganglioside mAbs.
Figure 10:
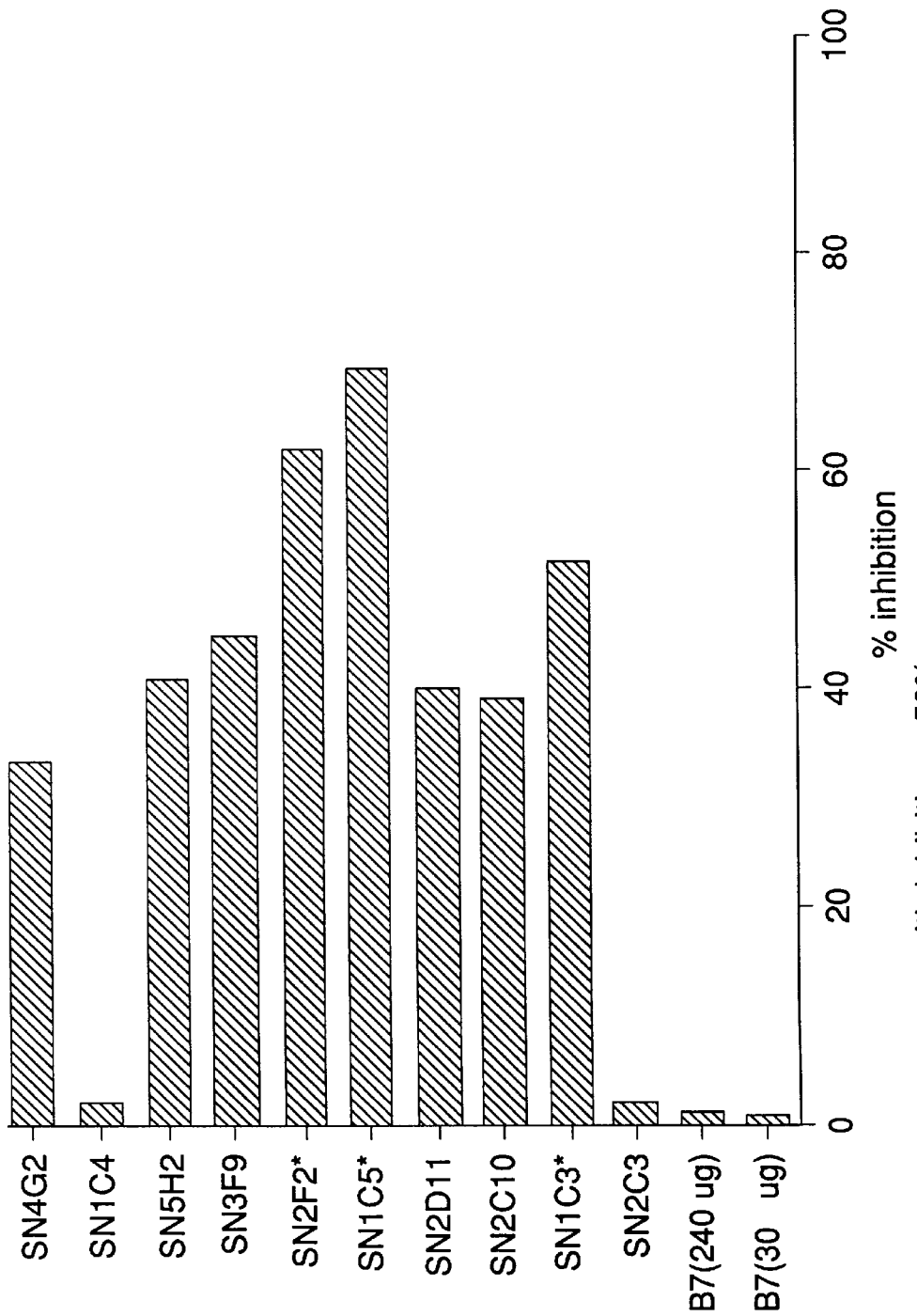
FIG. 10: shows the serological antibody response against NeuAcGM2 generated in a mouse immunized with the B7 anti-idE mAb. The antibody response was measured before and after the animal received the second and third doses of the mAb coupled to KLH.
Figure 11:
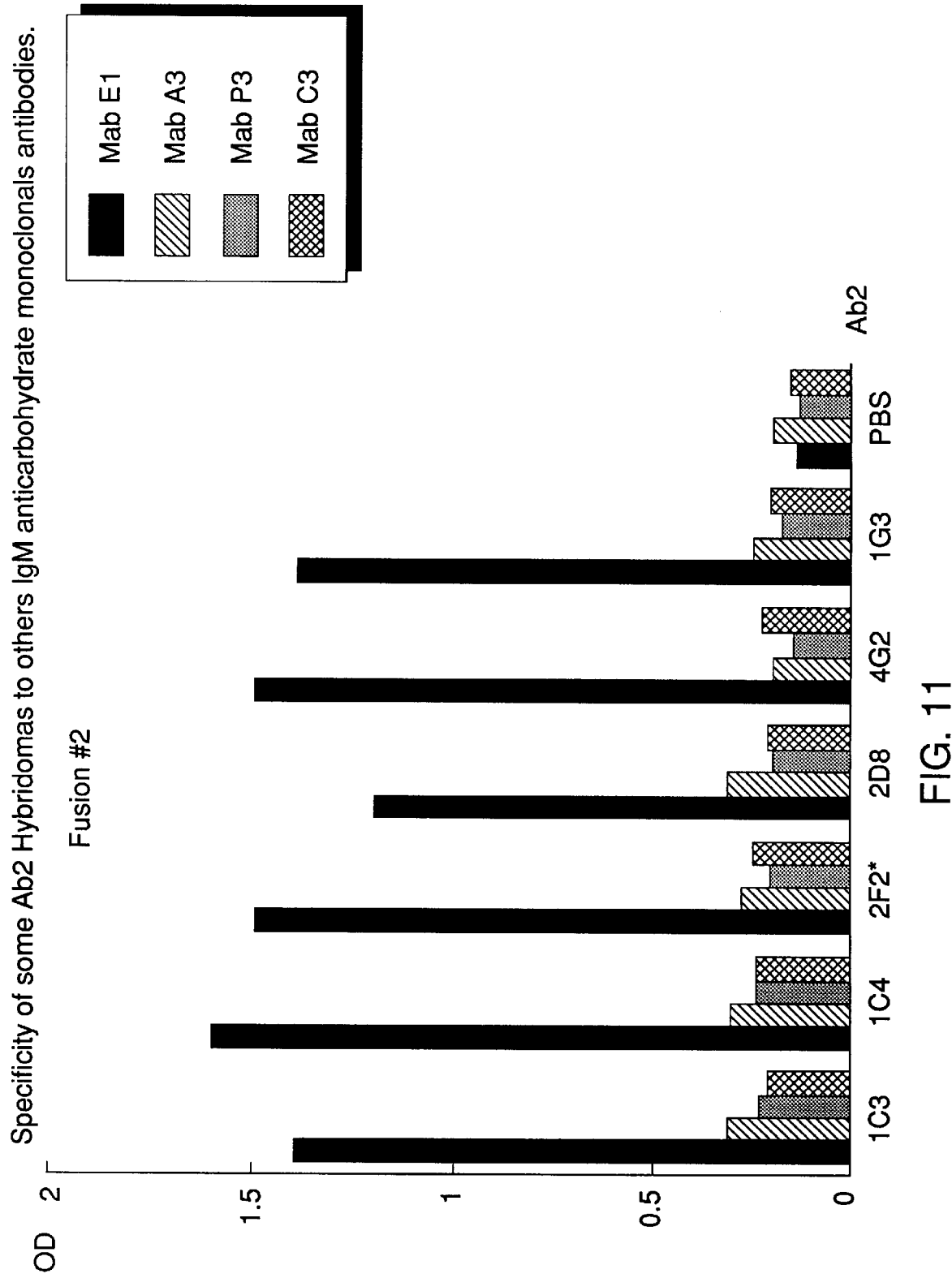
FIG. 11: is a bar graph showing the specificity of some Ab2 hybridomas to other IgM anti-carbohydrate monoclonal antibodies.
Figure 12:
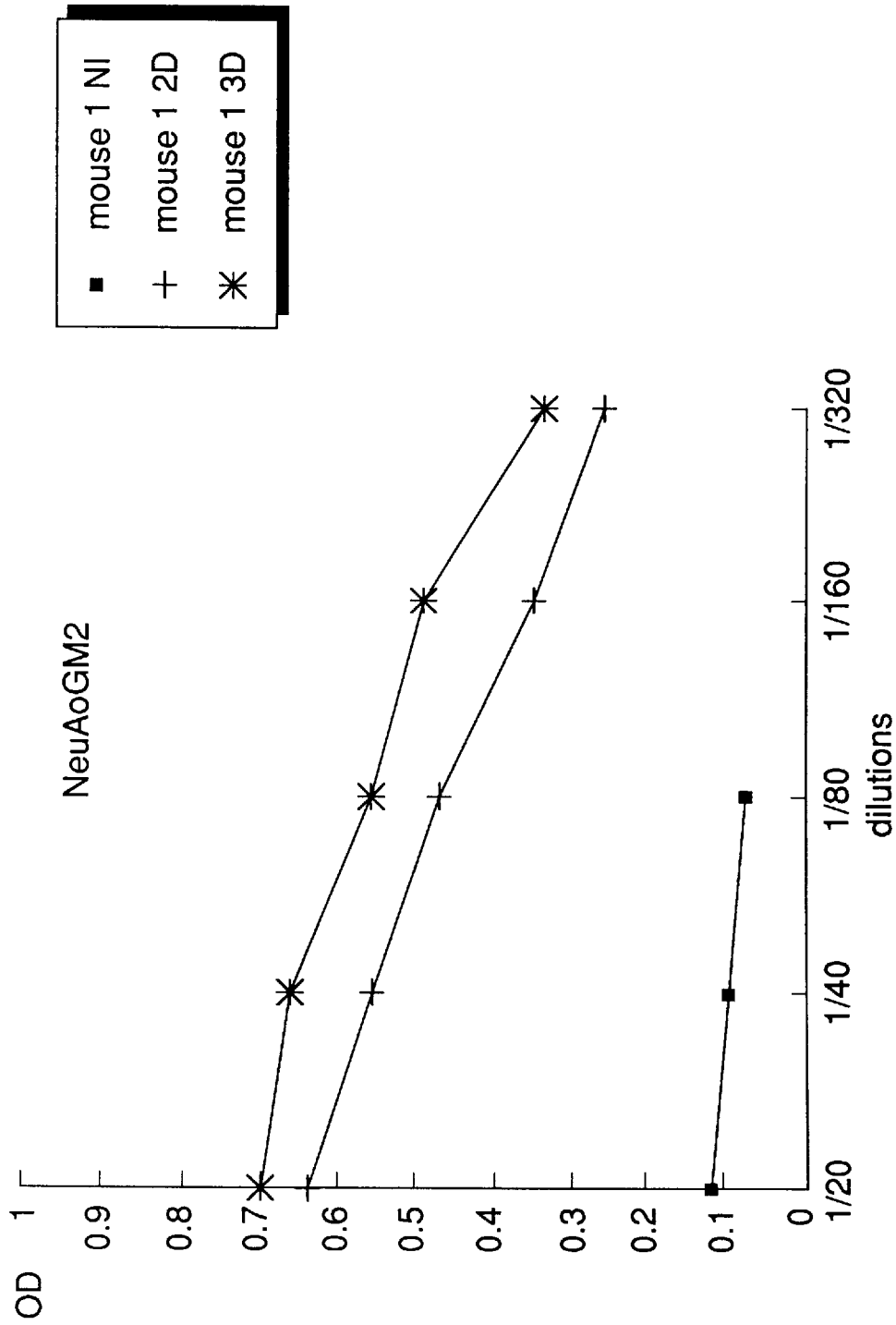
FIG. 12: is a graph depicting antibody response against NeuAcGM2 in a mouse immunized with anti-idE1 monoclonal antibody.

Table 1: shows the reactivities of A3, E1, F6 and P3 mAbs against different glycolipids as ascertained by ELISA and HPTLC-immuno-staining.

Table 2: shows the results of the immunohistochemical study of different malignant and benign human tissues using P3 mAb.

Table 3: shows the anti-idiotypic (Ab2) response obtained in a syngeneic model when Balb/c mice were immunized with three doses of 25 µg of the anti-ganglioside mAbs (A3, E1 and P3) injected alone or coupled to KLH at 15 days intervals.

TABLE 1

Reactivity of mAbs against different glycolipids

| GLYCOLIPIDS | mAb | | | |
|---|---|---|---|---|
| | A3 | E1 | F6 | P3 |
| NeuGcGM3 | − | − | − | +++ |
| NeuGcGM2 | − | − | − | +++ |
| GM3 | ++ | − | − | − |
| GM2 | +++ | ++ | − | − |
| GM1 | +++ | − | +++ | − |
| GD1a | − | − | − | − |
| GD1b | − | − | ++ | − |
| GD3 | − | − | − | − |
| GD2 | − | − | − | − |
| GT1b | − | − | − | − |
| Gg4Cer | − | − | + | − |
| LacCer | − | − | − | − |

+++ strong
++ moderate
+ weak
− negative

TABLE 2

Recognition pattern of P3 mAb in different malignant and benign tissues.

| Localization | Positives cases/total |
|---|---|
| BREAST | |
| Ductal infiltrating carcinoma | 12/12 |
| Lymph node metastases | 2/2 |
| Adenosis | 1/1 |
| LYMPH NODE | |
| Hyperplasia | 0/2 |
| Adenitis | 0/3 |
| Non HDG lymphoma | 0/2 |
| MUSCLE | |
| Leiomyosarcoma | 0/1 |
| PROSTATE | |
| Carcinoma | 0/1 |
| LUNG | |
| Adenocarcinoma | 0/2 |
| Carcinoma | 0/1 |
| THYROID | |
| Papillary carcinoma | 0/1 |
| Follicular carcinoma | 0/1 |
| COLON | |
| Normal | 0/1 |
| Hyperplastic polyp | 0/1 |
| Tubular adenoma | 0/1 |
| Tubulo-villious adenoma | 0/2 |
| Villious adenoma | 0/2 |
| Adenocarcinoma | 0/3 |
| Epidermoid carcinoma | 0/1 |
| OVARY | |
| Papillary cyto-adenocarcinoma | 0/1 |
| Serous cystoadenoma | 0/1 |
| Mucinous cystoadenoma | 0/1 |
| SKIN | |
| Normal | 0/1 |
| Basocellular carcinoma | 0/2 |
| Epidermoid carcinoma | 0/1 |
| Keratinized dermoid carcinoma | 0/1 |
| CENTRAL NERVOUS SYSTEM | |

TABLE 2-continued

Recognition pattern of P3 mAb in different malignant and benign tissues.

| Localization | Positives cases/total |
|---|---|
| Neurofibroma | 0/1 |
| Neurofibrosarcoma | 0/2 |
| Glyoblastoma | 0/1 |
| SOFT TISSUE | |
| Fusocelular sarcoma | 0/1 |

TABLE 3

Anti-Idiotypic response to Anti-Gangliosides antibodies

| mAb | # Responding mice | Specific Ab2 titer | Unspecific Ab2 titer |
|---|---|---|---|
| A3 Alone | 0/8 | 0 | 0 |
| A3 + KLH | 0/8 | 1/400000 | 0 (E1 and P3) |
| E1 alone | 0/6 | 0 | 0 |
| E1 + KLH | 5/6 | 1/20000 | 0 (A3 and P3) |
| P3 alone | 6/8 | 1/1000 | 0 (E1 and A3) |
| P3 + K1H | 8/8 | 1/50000 | 0 (E1 and A3) |
| Anti-ganglioside mAbs (1gM) | | | |

We claim:

1. IgM monoclonal antibodies with high specificity against gangliosides, characterized by having recurrent idiotypes, capable of binding specifically to the N-glycolyl neuraminic acid linked to a galactose of the gangliosides and having the characteristic, that alone or when coupled to a transporting protein and used for immunizing an animal, of connecting to the idiotypic network generating an Ab2 and Ab1' type antibody response; wherein said antibodies are produced by the cell line deposit number ECACC 94113026, deposited Nov. 30, 1994 with the Centre for Applied Microbiology and Research, Porton Down.

2. Monoclonal antibody according to claim 1 characterized by being capable of binding to the terminal tetrasaccharidic sequence Galβ1–3GalNAcβ1–4(NeuAcα2–3)Gal.

3. Monoclonal antibody according to claim 1 characterized by being capable of binding to the trisaccharidic sequence GalNAcβ1–4(NeuAcα2–3)Gal in the NeuAcGM2 and NeuAcGM1 gangliosides.

4. Monoclonal antibody according to claim 1 capable of specifically reacting with the terminal galactosamine and the N-acetyl neuraminic acid linked to the internal galactose of the NeuAcGM2 ganglioside.

5. Monoclonal antibody according to claim 1 capable of binding specifically to the N-glycolyl neuraminic acid linked to the internal galactose of the gangliosides.

6. Hybridomas producing monoclonal antibodies according to claim 1 generated by fusion of murine myeloma cell lines with splenocytes of immunize mice.

7. Hybridoma producing monoclonal antibody according to claim 1.

8. A pharmaceutical composition, comprising effective quantities of a monoclonal antibody according to claim 1 along with a transporting molecule, a diluent or excipient.

9. A pharmaceutical composition according to claim 8, characterized by using the monoclonal antibody accoding to claim 5.

10. The monoclonal antibody of claim 1, which is capable of binding specifically to gangliosides which comprise the structure NeuGc α2>3Gal, independently of the structure's terminal or internal position.

11. The monoclonal antibody of claim 10, which, alone or when coupled to a transporting protein and used for immunizing an animal, generates an Ab2 and Ab1' type antibody response.

12. A hybridoma which produces a monoclonal antibody according to claim 10.

13. The hybridoma of claim 12 which produces a monoclonal antibody, which, alone or when coupled to a transporting protein and used for immunizing an animal, generates an Ab2 and Ab1' type antibody response.

14. A reagent for the detection of tumor cells which express gangliosides, said reagent comprising a monoclonal antibody as claimed in claim 10 coupled to a marker.

15. The reagent of claim 14 wherein said monoclonal antibody, alone or when coupled to a transporting protein and used for immunizing an animal, generates an Ab2 and Ab1' type antibody response.

16. A pharmaceutical composition comprising the monoclonal antibody of claim 10, together with a transporting molecule, a diluent or an excipient.

17. The pharmaceutical composition of claim 16 wherein said monoclonal antibody, alone or when coupled to a transporting protein and used for immunizing an animal, generates an Ab2 and Ab1' type antibody response.

18. The monoclonal antibody of claim 10, which is capable of binding specifically to gangliosides selected from the group consisting of GM2 and GM3.

19. The monoclonal antibody of claim 10, which binds specifically to N-glycolyl residues.

* * * * *